US008826745B2

(12) United States Patent
Van Cleve (10) Patent No.: US 8,826,745 B2
(45) Date of Patent: Sep. 9, 2014

(54) VIBRATORY FLOW METER AND METHOD FOR DETERMINING VISCOSITY IN A FLOW MATERIAL

(75) Inventor: Craig Brainerd Van Cleve, Lyons, CO (US)

(73) Assignee: Micro Motion, Inc., Boulder, CO (US)

( * ) Notice: Subject to any disclaimer, the term of this patent is extended or adjusted under 35 U.S.C. 154(b) by 676 days.

(21) Appl. No.: 12/529,654

(22) PCT Filed: Mar. 14, 2007

(86) PCT No.: PCT/US2007/064007
§ 371 (c)(1),
(2), (4) Date: Sep. 2, 2009

(87) PCT Pub. No.: WO2008/111983
PCT Pub. Date: Sep. 18, 2008

(65) Prior Publication Data
US 2010/0089174 A1    Apr. 15, 2010

(51) Int. Cl.
*G01F 1/84* (2006.01)
*G01F 15/02* (2006.01)
*G01N 9/00* (2006.01)
*G01N 11/16* (2006.01)

(52) U.S. Cl.
CPC ............ *G01F 1/8495* (2013.01); *G01F 1/8436* (2013.01); *G01F 1/8477* (2013.01); *G01F 15/024* (2013.01); *G01F 1/8413* (2013.01); *G01N 9/002* (2013.01); *G01N 11/16* (2013.01)
USPC ..................................... 73/861.357; 73/54.41

(58) Field of Classification Search
CPC ....................................................... G01F 1/84
USPC ............... 73/861.52, 861.61, 861.355, 54.05, 73/202, 54.01, 54.04, 54.11, 54.24–54.27, 73/861.351, 861.354, 861.357
See application file for complete search history.

(56) References Cited

U.S. PATENT DOCUMENTS

| 5,005,400 A | | 4/1991 | Lew |
| 5,297,426 A | * | 3/1994 | Kane et al. ...................... 73/202 |
| 5,661,232 A | * | 8/1997 | Van Cleve et al. ............ 73/54.05 |
| 5,734,112 A | * | 3/1998 | Bose et al. .................. 73/861.56 |

(Continued)

FOREIGN PATENT DOCUMENTS

| FR | 1474354 A | 3/1967 |
| JP | 11190650 A | 7/1999 |

(Continued)

*Primary Examiner* — Hezron E Williams
*Assistant Examiner* — Hoang Nguyen
(74) *Attorney, Agent, or Firm* — The Ollila Law Group LLC (57) ABSTRACT

A vibratory flow meter (5) for determining a viscosity of a flow material is provided according to the invention. The vibratory flow meter (5) includes a meter assembly (200) configured to generate a density (p) of a flow material, generate a first mass flow rate ($m_1$) for a first flowtube (210a), and a second mass flow rate ($m_2$) for a second flowtube (210b). The vibratory flow meter (5) further includes a restrictive orifice (252) located in the first flowtube (210a). The restrictive orifice (252) ensures that a first flow rate of the flow material in the first flowtube (210a) is less than a second flow rate of the flow material in the second flowtube (210b).

36 Claims, 8 Drawing Sheets

(56) References Cited

U.S. PATENT DOCUMENTS

| | | | |
|---|---|---|---|
| 5,861,561 A * | 1/1999 | Van Cleve et al. | 73/861.52 |
| 6,249,752 B1 * | 6/2001 | Cunningham et al. | 702/100 |
| 6,308,580 B1 * | 10/2001 | Crisfield et al. | 73/861.355 |
| 6,609,431 B1 * | 8/2003 | Tietsworth et al. | 73/861.52 |
| 7,694,584 B2 * | 4/2010 | Smith et al. | 73/861.354 |
| 7,716,995 B2 * | 5/2010 | Patten et al. | 73/861.355 |
| 7,845,242 B2 * | 12/2010 | McAnally et al. | 73/861.355 |
| 2009/0229377 A1 * | 9/2009 | Ushigusa et al. | 73/861.61 |
| 2009/0272173 A1 * | 11/2009 | McAnally et al. | 73/1.16 |

FOREIGN PATENT DOCUMENTS

| | | |
|---|---|---|
| KR | 20020001711 | 1/2002 |
| RU | 1817829 A3 | 5/1993 |
| RU | 2295120 C2 | 3/2007 |
| WO | 9319348 A2 | 9/1993 |
| WO | 0133174 | 5/2001 |

\* cited by examiner

VIBRATORY FLOW METER AND METHOD FOR DETERMINING VISCOSITY IN A FLOW MATERIAL

BACKGROUND OF THE INVENTION

1. Field of the Invention

The present invention relates to a vibratory flow meter, and more particularly, to a vibratory flow meter and method for determining viscosity in a flow material.

2. Statement of the Problem

Flow meters are widely used to measure the characteristics of flowing fluids, including gases and liquids. The characteristics can include a mass flow rate and a density, for example. The characteristics can further include a viscosity of the flow fluid. Viscosity is commonly defined as a measure of the resistance of a fluid to deformation under a shear stress. It can also be thought of as a resistance to flow or a fluid friction.

A viscosity measurement may be needed in many situations. A viscosity measurement may be needed when the end product is desired to have a predetermined viscosity. Examples are motor oils and other lubricants, where the viscosity of a produced or refined petroleum product may be required to fall within a predefined viscosity range. A viscosity measurement may be needed or required in the production of syrups and other food products. A viscosity may be needed in order to control or characterize an industrial process.

Viscometers exist. One type of viscometer is a rotation viscometer, wherein a body of some sort is rotated in a fluid. The force required to perform the rotation is measured and is used to derive the viscosity measurement. The rotation viscometer has drawbacks, however. Foremost is that the fluid sample must be removed from the process pipeline in order to measure its viscosity. Also, various fluids may exhibit a great range in viscosity as much as four orders of magnitude in some cases. Therefore, a rotation viscometer may perform well at some viscosities but may not be best suited for measuring viscosity of certain fluids and may not perform well at higher or lower viscosities. A rotation viscometer may present problems in applications where the device needs to be cleaned and cannot retain the flow material, such as in the food industry or in the chemical or semiconductor industries.

Coriolis meters and vibratory densimeters operate by vibrating one or more flowtubes that are conducting a flow material. Such vibratory flow meters advantageously do not restrict a flow during operation. In addition, such vibratory flow meters comprise essentially smooth and uninterrupted conduits that are easy to empty and easy to clean. This offers advantages in many flow measuring environments.

SUMMARY OF THE SOLUTION

A vibratory flow meter for determining a viscosity of a flow material is provided according to an embodiment of the invention. The vibratory flow meter comprises a meter assembly configured to generate a density ($\rho$) of a flow material, generate a first mass flow rate ($\dot{m}_1$) for a first flowtube, and a second mass flow rate ($\dot{m}_2$) for a second flowtube. The vibratory flow meter further comprises a restrictive orifice located in the first flowtube. The restrictive orifice ensures that a first flow rate of the flow material in the first flowtube is less than a second flow rate of the flow material in the second flowtube.

A vibratory flow meter for determining a viscosity of a flow material is provided according to an embodiment of the invention. The vibratory flow meter comprises a first flowtube receiving a first portion of a flow material as a first flow, a second flowtube receiving a second portion of the flow material as a second flow, and a common driver that is configured to substantially simultaneously vibrate the first flowtube and the second flowtube. The vibratory flow meter further comprises three pickoff sensors configured to generate a first vibrational response from the first flowtube and a second vibrational response from the second flowtube. One of the three pickoff sensors is shared between the first flowtube and the second flowtube. The vibratory flow meter further comprises a restrictive orifice located in the first flowtube. The restrictive orifice is smaller than a local flowtube diameter and the restrictive orifice ensures that the first flow is different from the second flow.

A vibratory flow meter for determining a viscosity of a flow material is provided according to an embodiment of the invention. The vibratory flow meter comprises a first flowtube receiving a first portion of a flow material as a first flow, a second flowtube receiving a second portion of the flow material as a second flow, and a common driver configured to substantially simultaneously vibrate the first flowtube and the second flowtube. The vibratory flow meter further comprises three or more pickoff sensors configured to generate a first vibrational response from the first flowtube and a second vibrational response from the second flowtube. The vibratory flow meter further comprises a removable orifice member located in the first flowtube and including a restrictive orifice. The restrictive orifice is smaller than a local flowtube diameter and the restrictive orifice ensures that the first flow is different from the second flow.

A vibratory flow meter for determining a viscosity of a flow material is provided according to an embodiment of the invention. The vibratory flow meter comprises a first flowtube receiving a first portion of a flow material as a first flow, a second flowtube receiving a second portion of the flow material as a second flow, and a common driver configured to substantially simultaneously vibrate the first flowtube and the second flowtube. The vibratory flow meter further comprises three or more pickoff sensors configured to generate a first vibrational response from the first flowtube and a second vibrational response from the second flowtube. The vibratory flow meter further comprises a controllable orifice member that provides an adjustable restrictive orifice in communication with the first flowtube. The adjustable restrictive orifice is smaller than a local flowtube diameter and the controllable orifice member therefore ensures that the first flow is different from the second flow. The controllable orifice member is controllable to achieve a plurality of orifice configurations.

A method of determining a viscosity of a flow material in a vibratory flow meter is provided according to an embodiment of the invention. The method comprises partially restricting a first flowtube with a restrictive orifice. The first flowtube conducts a first flow of a flow material and the second flowtube conducts a second flow of the flow material. The second flow is different from the first flow. The method further comprises vibrating a first flowtube of the vibratory flow meter with a driver and generating a first vibrational response and substantially simultaneously vibrating a second flowtube of the vibratory flow meter with the driver and generating a second vibrational response. The method further comprises determining a viscosity of the flow material from the first vibrational response and the second vibrational response.

ASPECTS

In one aspect of the vibratory flow meter, the restrictive orifice is selected for a predetermined flow material viscosity range.

In another aspect of the vibratory flow meter, the vibratory flow meter comprises a viscometer.

In yet another aspect of the vibratory flow meter, the flow meter further comprises a second restrictive orifice located in the second flowtube, with the second restrictive orifice being different from the restrictive orifice.

In yet another aspect of the vibratory flow meter, the flow meter further comprises meter electronics coupled to the meter assembly and configured to receive a first vibrational response from the first flowtube, receive a second vibrational response from the second flowtube, and determine the flow material density ($\rho$), the first mass flow rate ($\dot{m}_1$), and the second mass flow rate ($\dot{m}_{12}$) from the first vibrational response and the second vibrational response.

In yet another aspect of the vibratory flow meter, the flow meter further comprises determining the viscosity of the flow material from the flow material density ($\rho$), the first mass flow rate ($\dot{m}_1$) of the first flow, and the second mass flow rate ($\dot{m}_2$) of the second flow.

In yet another aspect of the vibratory flow meter, the restrictive orifice is substantially fixed in the meter assembly.

In yet another aspect of the vibratory flow meter, the restrictive orifice is formed in a removable orifice member.

In yet another aspect of the vibratory flow meter, the restrictive orifice comprises an adjustable restrictive orifice of a controllable orifice member.

In yet another aspect of the vibratory flow meter, the meter assembly comprises three or more pickoff sensors configured to generate a first vibrational response from the first flowtube and a second vibrational response from the second flowtube.

In yet another aspect of the vibratory flow meter, the meter assembly comprises three pickoff sensors configured to generate a first vibrational response from the first flowtube and a second vibrational response from the second flowtube, wherein one of the three pickoff sensors is shared between the first flowtube and the second flowtube.

In yet another aspect of the vibratory flow meter, the flow meter further comprises meter electronics coupled to the three pickoff sensors and configured to receive the first vibrational response from the first flowtube, receive the second vibrational response from the second flowtube, and determine a viscosity of the flow material from the first vibrational response and the second vibrational response.

In yet another aspect of the vibratory flow meter, the flow meter further comprises meter electronics coupled to the three or more pickoff sensors and configured to receive the first vibrational response from the first flowtube, receive the second vibrational response from the second flowtube, and determine a viscosity of the flow material from the first vibrational response and the second vibrational response.

In yet another aspect of the vibratory flow meter, one of the three or more pickoff sensors is shared between the first flowtube and the second flowtube.

In yet another aspect of the vibratory flow meter, the flow meter further comprises a second controllable orifice member in communication with the second flowtube and including a second adjustable restrictive orifice, with the second adjustable restrictive orifice being different from the adjustable restrictive orifice.

In one aspect of the method, the vibratory flow meter includes a restrictive orifice located in the first flowtube that is smaller than a local flowtube diameter and with the restrictive orifice ensuring that the first flow is different from the second flow.

In another aspect of the method, the restrictive orifice is selected for a predetermined flow material viscosity range.

In yet another aspect of the method, the vibratory flow meter comprises a viscometer.

In yet another aspect of the method, the method further comprises a second restrictive orifice located in the second flowtube, with the second restrictive orifice being different from the restrictive orifice.

In yet another aspect of the method, determining the viscosity of the flow material from the first vibrational response and the second vibrational response comprises determining the viscosity from a flow material density ($\rho$), a first mass flow rate ($\dot{m}_1$) of the first flow, and the second mass flow rate ($\dot{m}_2$) of the second flow.

In yet another aspect of the method, the restrictive orifice is substantially fixed in the meter assembly.

In yet another aspect of the method, the restrictive orifice is formed in a removable orifice member.

In yet another aspect of the method, the restrictive orifice comprises an adjustable restrictive orifice of a controllable orifice member.

In yet another aspect of the method, the vibratory flow meter comprises three or more pickoff sensors configured to generate the first vibrational response and the second vibrational response, wherein one of the three or more pickoff sensors is shared between the first flowtube and the second flowtube.

DETAILED DESCRIPTION OF THE INVENTION

FIGS. 1-10 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
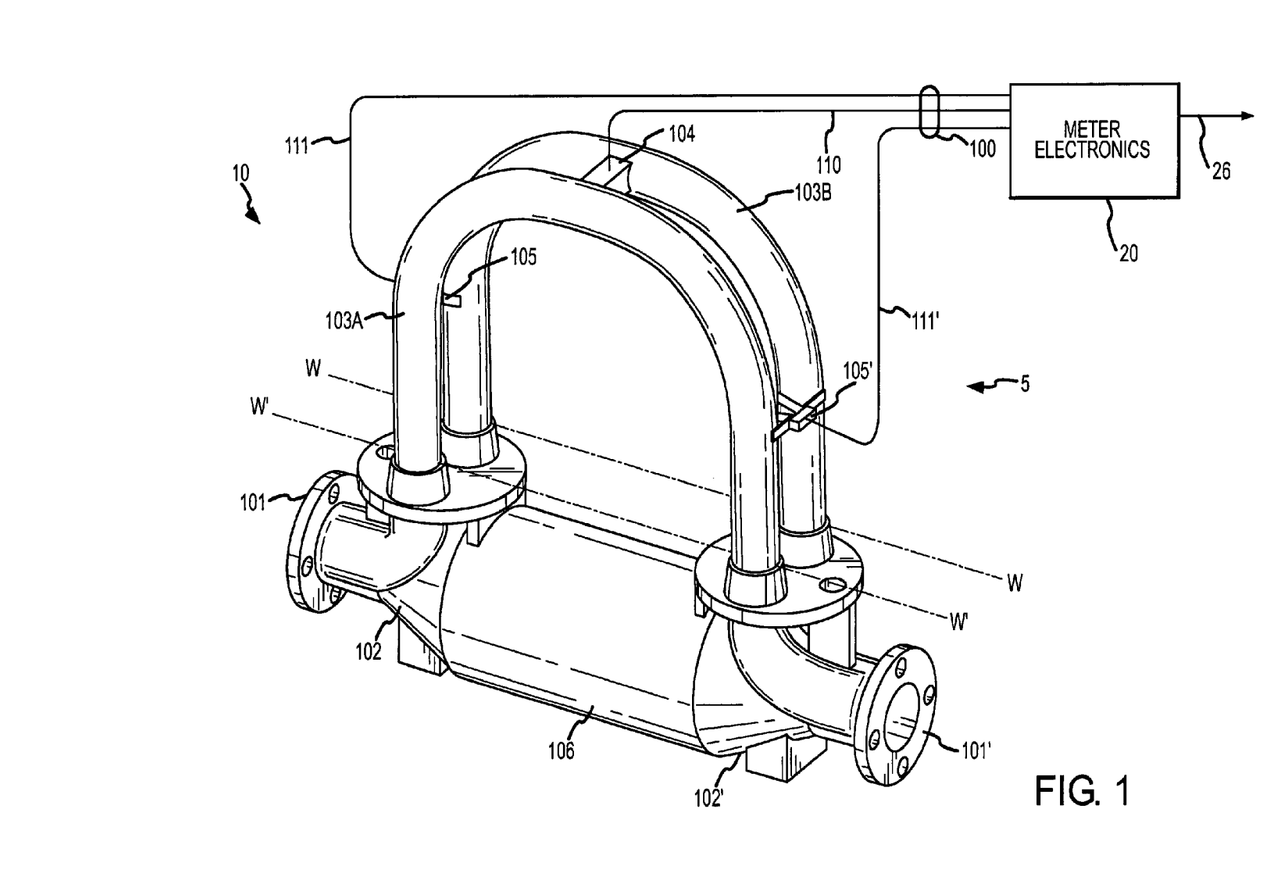
FIG. 1 shows a Coriolis flow meter comprising a meter assembly and meter electronics.

FIG. 1 illustrates a flow meter 5 comprising a flow meter assembly 10 and meter electronics 20. Meter electronics 20 is connected to meter assembly 10 via leads 100 to provide density, mass flow rate, volume flow rate, totalized mass flow, temperature, and other information over path 26. It should be apparent to those skilled in the art that the present invention can be used in any type of Coriolis flow meter regardless of the number of drivers, pick-off sensors, flow conduits, or the operating mode of vibration. In addition, it should be recognized that the flow meter 5 can alternatively comprise a vibratory densitometer.

Flow meter assembly 10 includes a pair of pipeline flanges 101 and 101', manifolds 102 and 102', driver 104, pick-off sensors 105-105', and flow conduits 103A and 103B. Driver 104 and pick-off sensors 105 and 105' are connected to flow conduits 103A and 103B.

Pipeline flanges 101 and 101' are affixed to manifolds 102 and 102'. Manifolds 102 and 102' can be affixed to opposite ends of a spacer 106. Spacer 106 maintains the spacing between manifolds 102 and 102' to prevent undesired stresses in flow conduits 103A and 103B due to pipeline forces. When flow meter assembly 10 is inserted into a conduit system (not shown) which carries the material being measured, material enters flow meter assembly 10 through the pipeline flange 101, passes through inlet manifold 102 where the total amount of material is directed to enter flow conduits 103A and 103B, flows through flow conduits 103A and 103B and back into outlet manifold 102' where it exits meter assembly 10 through the pipeline flange 101'.

Flow conduits 103A and 103B are selected and appropriately mounted to inlet manifold 102 and outlet manifold 102' so as to have substantially the same mass distribution, moments of inertia, and elastic modules about bending axes W-W and W'-W' respectively. The flow conduits extend outwardly from the manifolds in an essentially parallel fashion.

Flow conduits 103A and 103B are driven by driver 104 in opposite directions about their respective bending axes W and W' and at what is termed the first out of phase bending mode of the flow meter. Driver 104 may comprise one of many well known arrangements, such as a magnet mounted to flow conduit 103A and an opposing coil mounted to flow conduit 103B. An alternating current is passed through the opposing coil to cause both conduits to oscillate. A suitable drive signal is applied by meter electronics 20, via lead 110 to driver 104.

Meter electronics 20 receives sensor signals on leads 111 and 111', respectively. Meter electronics 20 produces a drive signal on lead 110 which causes driver 104 to oscillate flow conduits 103A and 103B. Meter electronics 20 processes left and right velocity signals from pick-off sensors 105 and 105' in order to compute a mass flow rate. Path 26 provides an input and an output means that allows meter electronics 20 to interface with an operator or with other electronic systems. The description of FIG. 1 is provided merely as an example of the operation of a Coriolis flow meter and is not intended to limit the teaching of the present invention.

Figure 2:
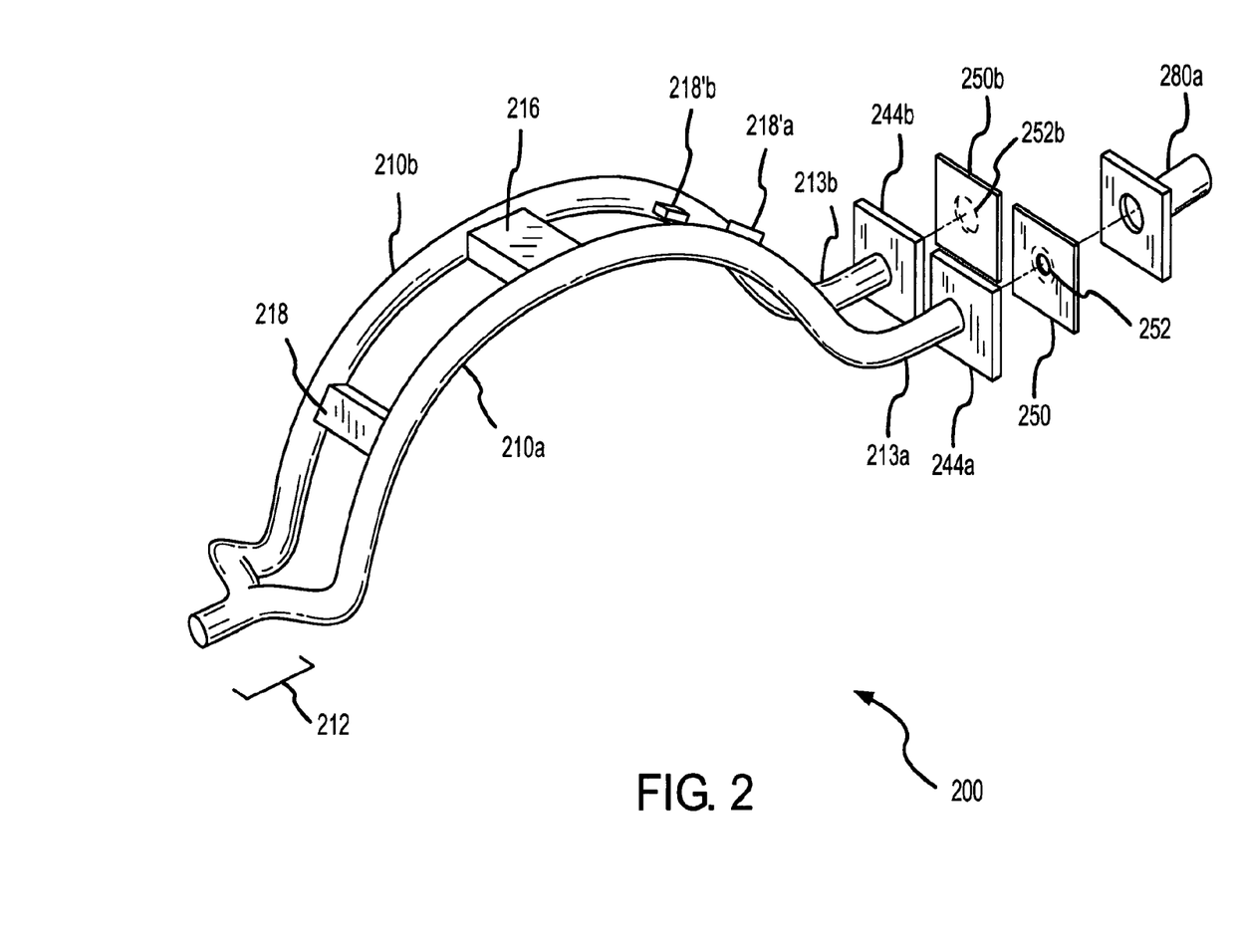
FIG. 2 shows a vibratory flow meter according to an embodiment of the invention.

FIG. 2 shows a meter assembly 200 according to an embodiment of the invention. The meter assembly 200 can replace the meter assembly 10 of FIG. 1 in the vibratory flow meter 5, wherein the meter assembly 200 can be connected to the meter electronics 20. The flow meter 5 including the meter assembly 200 comprises a viscometer that provides a viscosity determination for a flow material. However, it should be understood that the flow meter 5 can additionally provide mass flow measurements, including mass flow measurements through individual flowtubes ($\dot{m}_1$ and $\dot{m}_2$) and a density measurement ($\rho$) of the flow material. As a result, the flow meter 5 can additionally comprise a vibrating densitometer and/or a Coriolis flow meter. Other additional flow measurements can be generated and are within the scope of the description and claims.

The meter electronics 20 in one embodiment is configured to vibrate the first flowtube 210a conducting a first flow and vibrate a second flowtube 210b conducting a second flow, with the vibrating being performed by the common driver 216. The meter electronics 20 further receives a first vibrational response from the first flowtube 210a, receives a second vibrational response from the second flowtube 210b, and determines a viscosity from the first vibrational response and the second vibrational response. In addition, the meter electronics 20 may further determine mass flow rates and a density of the first flow and the second flow. The viscosity can therefore be determined from a first mass flow rate ($\dot{m}_1$) of the first flowtube 210a, a second mass flow rate ($\dot{m}_2$) of the second flowtube 210b, and the flow material density ($\rho$).

One common problem in measuring viscosity arises from the great range in viscosity of fluids. The viscosity can vary by as much as four orders of magnitude. The flow fluid has to flow through the meter at a high enough rate that the meter can accurately measure the fluid, and yet at a low enough rate that the pressure drop through the meter is not excessive.

In some embodiments, the first flow and the second flow are in a substantially laminar flow regime. A flow material of a relatively high viscosity will possess a laminar flow during low fluid flow. As a result, the flow material in the flowtubes is substantially smooth and undisturbed and the pressure drop is high. For laminar flow, the restrictive orifice may need to be significantly smaller than a local flowtube size so as to have a high enough pressure drop to cause a significant difference in flow rates.

In other embodiments, the first flow and the second flow are in a substantially turbulent flow regime. A low viscosity flow material will exhibit a turbulent flow at a measurable flow rate, such as at a relatively high flow rate and under a relatively low pressure. As a result, the flow material in the first flowtube and in the second flowtube will have a relatively low pressure drop even without the presence of a restrictive orifice. For turbulent flow, the restrictive orifice will need to be only slightly smaller than the local flowtube size.

Unfortunately, the pressure drop equations for the laminar and turbulent flow regimes are different. Therefore, an optimal flow restrictor for the laminar flow regime is not optimal for the turbulent flow regime. Therefore, it has been problematic to design a viscosity measuring meter that can accommodate both low and high viscosity fluids and fluids in between.

The solution to the problem is to optimize the set of parameters separately for each flow regime and have an appropriate flow restrictor for a desired viscosity or viscosity range. The solution can include employing a removable orifice member. As a result, an appropriate restrictive orifice can be selected through the selection of a removable orifice member and can be used to configure the flow meter. The flow restrictor provides an additional pressure drop in the flow path. The pressure drop is proportional to the dissipated kinetic energy of the fluid. A restrictive orifice of smaller diameter/size than the corresponding flowtube causes the fluid velocity to increase. The excess velocity is dissipated downstream as turbulence. The pressure drop caused by this energy dissipation is the only pressure drop term in the pressure equation that is independent of viscosity. Without this term (using, for example, a venturi instead of an orifice), viscosity cancels out of the pressure equations. As a result, the flow ratio in a meter with a venturi in one flow tube as the flow restricting device is independent of viscosity and cannot be used to determine viscosity.

The meter assembly 200 includes a first flowtube 210a and a second flowtube 210b. The first and second flowtubes 201a and 210b in this embodiment originate from a common inlet 212 and have independent first and second outlets 213a and 213b. The two flowtubes 210a and 210b can include flanges at the intake end (see FIGS. 9-11). The two flowtubes 210a and 210b include flanges 244a and 244b at the outlet end. The meter assembly 200 can alternatively receive separate input flows and does not require an input manifold that splits an input into two streams. However, in order to determine viscosity, the flow material in the conduits must be the same and must be provided at the same pressure at the inlet. Likewise, the output of the meter assembly 200 can comprise a combined flow stream or can comprise two independent flow streams that have the same pressures at the outlet.

In one embodiment, the flowtubes 210a and 210b comprise substantially U-shaped flowtubes, as shown. Alternatively, in an embodiment shown in FIG. 10 and discussed below, the flowtubes 210a and 210b can comprise substantially straight flowtubes. However, other shapes can also be used, and are within the scope of the description and claims.

A common driver 216 is located between the first flowtube 210a and the second flowtube 210b. The common driver 216 is configured to simultaneously vibrate the first and second flowtubes 210a and 210b.

The meter assembly 200 can include three or four pickoff sensors 218. The pickoff sensors 218 are coupled to the meter electronics 20 by the leads 100 (not shown). Consequently, the vibrational responses from the pickoff sensors are received and processed by the meter electronics 20.

In a first embodiment, a shared pickoff sensor 218 is located between the first flowtube 210a and the second flowtube 210b. The shared pickoff sensor 218 is configured to generate a shared vibrational response from vibration of both the first flowtube 210a and the second flowtube 210b. The shared pickoff sensor 218 can comprise either an upstream pickoff sensor or a downstream pickoff sensor.

A first independent pickoff sensor 218'a is coupled to the first flowtube 210a and is configured to generate a first independent vibrational response from vibration of the first flowtube 210a. A second independent pickoff sensor 218'b is coupled to the second flowtube 210b and is configured to generate a second independent vibrational response from vibration of the second flowtube 210b. The first and second independent pickoff sensors 218'a and 218'b can be supported by any manner of rigid support structure (not shown), wherein the first and second independent pickoff sensors 218'a and 218'b are held in a fixed position by the support structure and measure motion of the vibration of the corresponding flowtubes. Each of the independent pickoff sensors 218'a and 218'b therefore generates a vibrational response for a single flowtube, independent of the other flowtube (and independent of the other flow stream).

The meter assembly 200 includes a restrictive orifice 252 located in the first flowtube 210a. In the embodiment shown in the figure, the restrictive orifice 252 is implemented in and provided by a removable orifice member 250 (see also FIGS. 4-5). However, the meter assembly 200 can alternatively employ a restrictive orifice 252 that is substantially fixed in a flowtube 210 (see FIG. 6 and the accompanying text) or can employ a controllable orifice member 290 (see FIGS. 7-8 and the accompanying text).

The figure shows a removable orifice member 250 including the restrictive orifice 252. The restrictive orifice 252 is positioned between the flow passage of the first flowtube 210a and the corresponding flow passage of the output manifold 280a. The removable orifice member 250 can be clamped, trapped, or otherwise held between an outlet flange 244 and the output manifold 280. Although the restrictive orifice 252 is shown at an outlet of a flowtube, it should be understood that the restrictive orifice 252 can be positioned at any point in a flowtube wherein the restrictive orifice 252 reduces the flow rate in the affected flowtube.

Only one output manifold 280 is shown, but it should be understood that both flanges 244a and 244b can attach to one or more respective output manifolds as long as the meter assembly 200 maintains, in the two manifolds, substantially equal upstream pressures and downstream pressures. Alternatively, the removable orifice member 250 can be received in any manner of receptacle, socket, etc.

The restrictive orifice 252 can be of a predetermined size and can be of a predetermined shape. The difference in size can be selected according to characteristics of the flow material, including the viscosity of the flow material. The restrictive orifice 252 can be selected for a predetermined flow material viscosity range. The restrictive orifice 252 is smaller in size than a local flowtube diameter (see dashed line). The restrictive orifice 252 therefore restricts flow in the first flowtube 210a and makes the flow rate of the first flow in the first flowtube 210a less than the flow rate of the second flow in the second flowtube 210b.

The restrictive orifice 252 causes a loss of kinetic energy in the first flowtube 210a. The lost kinetic energy comprises turbulence in the flow. The kinetic energy is not recovered, as is true of a venturi. The term venturi as used herein may be defined as a section of a flow channel which contains a reduction in flow area followed by a gradual increase in flow area such that most of the total fluid pressure is conserved, wherein the static fluid pressure is converted to dynamic pressure and then back to static pressure.

The basic equation for pressure loss ($\Delta P$) through an orifice comprises:

$$\Delta P = K \frac{\rho(V_0^2 - V_1^2)}{2} \tag{1}$$

Where $\Delta P$ is the change in pressure due to the orifice, K is the kinetic energy dissipation coefficient, $\rho$ is the density of the flow fluid, $V_1$ is the flow velocity in the first flowtube 210a, and $V_0$ is the flow velocity through the orifice.

The above equation represents a total pressure drop due to the kinetic energy that is dissipated through (and after) the orifice. It should be noted that the dissipation coefficient (K) is a function of the orifice diameter ratio ($\beta$). The orifice diameter ratio ($\beta$) comprises a ratio of the orifice diameter ($d_0$) to the tube diameter ($d_1$) of the first flowtube 210a.

$$K = 1 - 0.24\beta - 0.52\beta^2 - 0.16\beta^3 \tag{2}$$

The basic equation for pressure drop in a flow tube can be determined by the Darcy formula:

$$\Delta P = f \frac{l}{d} \frac{\rho V^2}{2} \tag{3}$$

Where (f) is the friction factor of the pipe, (l) is the length of the tube, and (d) is the tube diameter.

For a laminar fluid flow, the friction factor (f) can be expressed as:

$$f_{lam} = \frac{64}{Re} = \frac{64\mu}{\rho V d} \tag{4}$$

Where (Re) is the Reynolds number and ($\mu$) is the fluid viscosity. Therefore, the pressure drop ($\Delta P$) in a tube for laminar flow comprises:

$$\Delta P_{lam} = \frac{64\mu}{\rho V d} \frac{l}{d} \frac{\rho V^2}{2} = \frac{32\mu l V}{d^2} \quad (5)$$

For a turbulent fluid flow, the pressure drop ($\Delta P$) can again be expressed by the Darcy formula:

$$\Delta P = f \frac{l}{d} \frac{\rho V^2}{2} \quad (6)$$

But for turbulent flow, the friction factor (f) has the form:

$$f_{turb} = \frac{0.316}{Re^{\frac{1}{4}}} \quad (7)$$

This turns the Darcy formula into:

$$\Delta P_{turb} = \frac{.316 \mu^{\frac{1}{4}} l \rho^{\frac{3}{4}} V^{\frac{7}{4}}}{2 d^{\frac{5}{4}}} \quad (8)$$

Because the two flow paths through the meter assembly 200 come from a common upstream pressure and join at a common downstream pressure, the pressure drops through the two flow paths have to be equal. Thus, a second flowtube pressure drop ($\Delta P_2$) can be assumed to be equal to a first flowtube pressure drop ($\Delta P_1$). The flow rates through the two flowtubes 210a and 210b are not equal, however, because one flowtube contains the restrictive orifice 252.

$$\Delta P_1 = \Delta P_2 \quad (9)$$

Consequently, equation (9) can be transformed into a laminar flow regime viscosity equation comprising:

$$\mu_{lam} = \left(\frac{K\rho d^2}{64l}\right) \times \left(\frac{V_0^2 - V_1^2}{V_2 - V_1}\right) \quad (10)$$

The flow velocity terms can be derived from the mass flow rate and density measurements obtained by the meter assembly 200, where:

$$\dot{m}_1 = \rho A_1 V_1 \quad (11)$$

$$\dot{m}_2 = \rho A_2 V_2 \quad (12)$$

The term (A) is the cross-sectional flow area of the flowtube. Consequently, the velocity $V_1$ of the flow material in the first flowtube 210a comprises:

$$V_1 = \frac{\dot{m}_1}{\rho A_1} \quad (13)$$

The velocity $V_2$ in the second flowtube 210b comprises:

$$V_2 = \frac{\dot{m}_2}{\rho A_2} \quad (14)$$

It should be understood that the flow velocity through the restrictive orifice 252, i.e., $V_0$, comprises:

$$V_0 = V_1 \times \frac{d_1^2}{d_0^2} \quad (15)$$

Where $d_1$ is the diameter of the first flowtube 210a and $d_0$ is the diameter of the restrictive orifice 252. In this example, the restrictive orifice 252 is located in the first flowtube 210a.

Likewise, equation (9) can be transformed into a turbulent flow regime viscosity equation comprising:

$$\mu_{turb} = \left[\frac{K d^{\frac{5}{4}} \rho^{\frac{1}{4}} (V_0^2 - V_2^2)}{.316 l \left(V_2^{\frac{3}{4}} - V_1^{\frac{7}{4}}\right)}\right]^4 \quad (16)$$

Equation (16), along with equations (13-15) above, can be used in order to derive the viscosity in the turbulent flow regime from the measured values of the first mass flow rate ($\dot{m}_1$), the second mass flow rate ($\dot{m}_2$), and the flow material density ($\rho$).

In the embodiment shown, the first vibrational response comprises the shared vibrational response from the shared pickoff sensor 218 and the first independent vibrational response from the first independent pickoff sensor 218'a. A first flowtube time delay ($\Delta t_1$) comprises a phase difference between the shared vibrational response and the first independent vibrational response. The second vibrational response comprises the shared vibrational response and the second independent vibrational response from the second independent pickoff sensor 218'b. A second flowtube time delay ($\Delta t_2$) comprises a phase difference between the shared vibrational response and the second independent vibrational response. A time delay ($\Delta t$) therefore reflects a phase difference between an upstream vibrational response and a downstream vibrational response of a flowtube. The first flowtube time delay ($\Delta t_1$) and the second flowtube time delay ($\Delta t_2$) can be used by the meter electronics 20 to determine various flow stream characteristics for the meter assembly 200. For example, the first flowtube time delay ($\Delta t_1$) and the second flowtube time delay ($\Delta t_2$) can be used to determine first and second mass flow rates ($\dot{m}_1$) and ($\dot{m}_2$). The natural frequency of the vibrating tubes can also be processed in order to generate a density measurement ($\rho$).

The first flow stream of the meter assembly 200 must differ from the second flow stream. As a result, the first mass flow rate ($\dot{m}_1$) can be restricted to be less than the second mass flow rate ($\dot{m}_2$). Consequently, the flow through each flowtube can be measured independently of the flow through the other conduit.

In one embodiment, the flowtubes 210a and 210b comprise substantially U-shaped flowtubes, as shown. Alternatively, the flowtubes 210a and 210b can comprise substantially straight flowtubes (see FIG. 10). However, other shapes can also be used, and are within the scope of the description and claims.

The figure shows an optional second removable orifice member 250b (dashed lines). The second removable orifice member 250b can include a second restrictive orifice 252b. The second restrictive orifice 252b in the embodiment shown is approximately the same size as the second flowtube 210b. This can be done to maintain a uniform spacing between the meter assembly 200 and an output manifold 280, for example. Alternatively, the second removable orifice member 250b can comprise one component that includes both the restrictive orifice 252 and the second restrictive orifice 252b.

It should be understood that the second restrictive orifice 252b can be smaller than the second flowtube 210b. However, the second restrictive orifice 252b cannot generate a second mass flow rate ($\dot{m}_2$) that is equal to the first mass flow rate ($\dot{m}_1$). Consequently, the second restrictive orifice 252b must be different from the restrictive orifice 252.

By proper selection of the removable orifice plate 250, the meter assembly 200 can be configured according to a desired flow material. For example, if the flow material has a relatively low viscosity, i.e., the flow material has a low resistance to flow, then the restrictive orifice 252 is chosen to be relatively similar in size with regard to the inner diameter of the flowtube and the meter assembly 200 is operated in the turbulent flow regime. Correspondingly, if the viscosity is high, i.e., the flow material has a high resistance to flow, then the restrictive orifice 252 can be chosen to be relatively small in size (i.e., a large change in diameter) compared to the inner diameter of the flowtube as a large change in flow rate through the restrictive orifice 252 will be needed in order to create the desired kinetic energy loss.

The meter assembly 200 can measure a first mass flow rate ($\dot{m}_1$) for the first flowtube 210a and can independently measure a second mass flow rate ($\dot{m}_2$) for the second flowtube 210b. The meter assembly 200 takes advantage of the phase-locked loop of a drive algorithm. The drive algorithm can lock the phase between one of the pickoff sensors and the drive signal, using the phase-locked loop configuration. Conveniently, the shared pickoff sensor 218 can be locked to the drive signal for simplicity. By taking advantage of this locking feature in the pickoff sensor arrangement, it is possible to have a single pickoff sensor locked in phase to the drive signal and have two independent pickoff sensors, allowing two independent vibrational responses. The time delay ($\Delta t$) is measured between the locked pickoff sensor and each of the two independent pickoff sensors. In addition, the locked pickoff sensor can also comprise a reference feedback signal that is further used for generating the drive signal.

Although the flow through each flowtube is independent, the measurement of mass flow in one flowtube is not independent of the flow through the other conduit. A flow through one conduit induces a phase in the other conduit. Because of this linkage, a new mass flow equation is used for the two flowtubes of the three pickoff sensor meter assembly 200 according to the invention. The new dual flowtube equations are based on the time delay experienced by both flowtubes 210a and 210b (i.e., $\Delta t_1$ and $\Delta t_2$).

In a traditional dual tube Coriolis flow meter, a phase is measured between two flowtubes and a phase difference is calculated between inlet side pickoffs and outlet side pickoffs of the meter. This phase difference is converted into a single time delay ($\Delta t$) and is used to determine a flow amount (such as a mass flow rate $\dot{m}$, for example), by employing the equation:

$$\dot{m} = FCF \times (\Delta t - \Delta tz) \ast (1 - T_c \times T) \quad (17)$$

The $T_c$ and $T$ terms represent calibration and ambient temperature measurements, respectively. In this equation, a single measurement of time delay ($\Delta t$) can be used to measure flow. The time delay ($\Delta t$) is adjusted by a time delay at zero ($\Delta tz$). The time delay at zero ($\Delta tz$) comprises a calibration factor that is determined under no-flow conditions.

However, this traditional mass flow rate equation is not adequate for the two independent flowtubes of the three pickoff sensor meter assembly 200. The reason is that in the dual flowtubes of the invention, the flow induces some phase in both flowtubes. This is true even when there is flow in only one of the two flowtubes. In the traditional flow meter, because a common flow passes through both flowtubes, the induced phase is identical in each conduit. As a result, the induced phase does not appear as a phase difference between the two conduits and is not a factor in calculating a result. Therefore, a single time delay can be used in the prior art in order to determine a flow rate in a traditional flow meter.

In contrast, in the invention the first and second flow streams are independent. As a consequence, phase induced by the two flows may differ between the two flowtubes. Therefore, a mass flow rate equation based on a single time delay cannot be employed.

Flow in the three pickoff sensor meter assembly 200 induces phase in both flowtubes 210a and 210b, even though flow may only exist in one of the flowtubes. The two induced phases may differ. As a result, two time delay measurements are required from each flowtube in order to measure flow. The flow measurement can be for one or two flows. One illustration of this measurement scheme can be illustrated with the following equations:

$$\dot{m}_1 = FCF_{11}(\Delta t_{11} - \Delta tz_{11}) \times (1 - Tc_1 \times Tm_1) + FCF_{12}(\Delta t_{12} - \Delta tz_{12}) \times (1 - Tc_2 \times Tm_2) \quad (18)$$

$$\dot{m}_2 = FCF_{22}(\Delta t_{22} - \Delta tz_{22}) \times (1 - Tc_2 \times Tm_2) + FCF_{21}(\Delta t_{21} - \Delta tz_{21}) \times (1 - Tc_1 \times Tm_1) \quad (19)$$

where the subscript 1 refers to the first flowtube 210a and the subscript 2 refers to the second flowtube 210b. The second term in equations (18) and (19) (i.e., for the "2" of the $FCF_{12}$ term, for example) is required due to the fact that flow through one flow tube induces a phase in the other tube. Equations (18) and (19) can be used in the meter electronics 20 for determining mass flow rates in both flowtubes 210a and 210b.

Hereinafter, for time delay values of the form ($\Delta t_B^A$), the superscript A denotes which flowtube is conducting the flow. If flow is being conducted through the second flowtube 210b, then the time delay value will be of the form ($\Delta t_B^2$). The subscript B denotes the flowtube that a vibrational response is being received from. Therefore, the value ($\Delta t_2^1$) is the time delay measured for the second flowtube wherein the flow is through the first flowtube 210a. Alternatively, the value ($\Delta t_1^2$) is the time delay measured for the first flowtube 210a wherein the flow is through the second flowtube 210b. A superscript of zero denotes a no-flow condition, wherein the value ($\Delta t_1^0$) denotes a time delay measured for the first flowtube 210a wherein the first flowtube is vibrated by the common driver 216 under a zero or no-flow condition.

However, a simpler form of equations (18) and (19) can be used for determining the flow stream characteristics. Equations (18) and (19) do not take advantage of any symmetry. One possible form of symmetry is in the time delay. If the time delay is symmetric, i.e., if:

$$\Delta t_{11} \cong \Delta t_1 \quad (20a)$$

$$\Delta t_{12} \cong \Delta t_2 \quad (20b)$$

$$\Delta t_{21} \cong \Delta t_1 \quad (19c)$$

$$\Delta t_{22} \cong \Delta t_2 \quad (20d)$$

then equations (17) and (18) become:

$$\dot{m}_1 = FCF_{11}(\Delta t_1 - \Delta t z_1) \times (1 - Tc_1 \times Tm_1) + FCF_{12}(\Delta t_2 \Delta t z_2) \times (1 - Tc_2 \times Tm_2) \quad (21)$$

$$\dot{m}_2 = FCF_{22}(\Delta t_2 - tz_2) \times (1 - Tc_2 \times Tm_2) + FCF_{21}(\Delta t_1 - \Delta t z_1) \times (1 - Tc_1 \times Tm_1) \quad (22)$$

The T terms represent temperature measurements. The $Tc_1$ term is the temperature of the first flowtube 210a and the $Tm_1$ term is the temperature of the first flow fluid. Likewise, the $Tc_2$ term is the temperature of the second flowtube 210b and the $Tm_2$ term is the temperature of the second flow fluid. The $(\Delta tz_1)$ value is the zero flow calibration value for the first flowtube 210a and the $(\Delta tz_2)$ value is the zero flow calibration value for the second flowtube 210b. The flow calibration factors $FCF_{11}$, $FCF_{12}$, $FCF_{21}$, and $FCF_{22}$ are calibration coefficients that are determined by flow tests and subsequently are used in flow stream characteristic calibrations.

Additionally, the flow calibration factors could also be symmetric. In this case, equations (21) and (22) would be further simplified by the fact that the flow calibration factors may be approximately symmetrical, i.e., $FCF_{12} \approx FCF_{21}$. The symmetry of the equations would influence the calibration process.

The ability to measure two mass flow rates may also make it possible to measure additional process variables beyond just the two mass flow rates. For instance, if one of the flowtubes contains a restrictive orifice, the ratio of the two flow rates can be related to dynamic viscosity. Another potential application would be the measurement of coating on the interior surfaces of the flowtubes. Such flowtube coating will induce an unbalanced mass in the system and this unbalanced mass may be detectable through a ratio of amplitudes of the two resulting flowtube vibrational responses. These are just two examples of what may be feasible with a flow meter that measures two independent flow streams.

Figure 3:
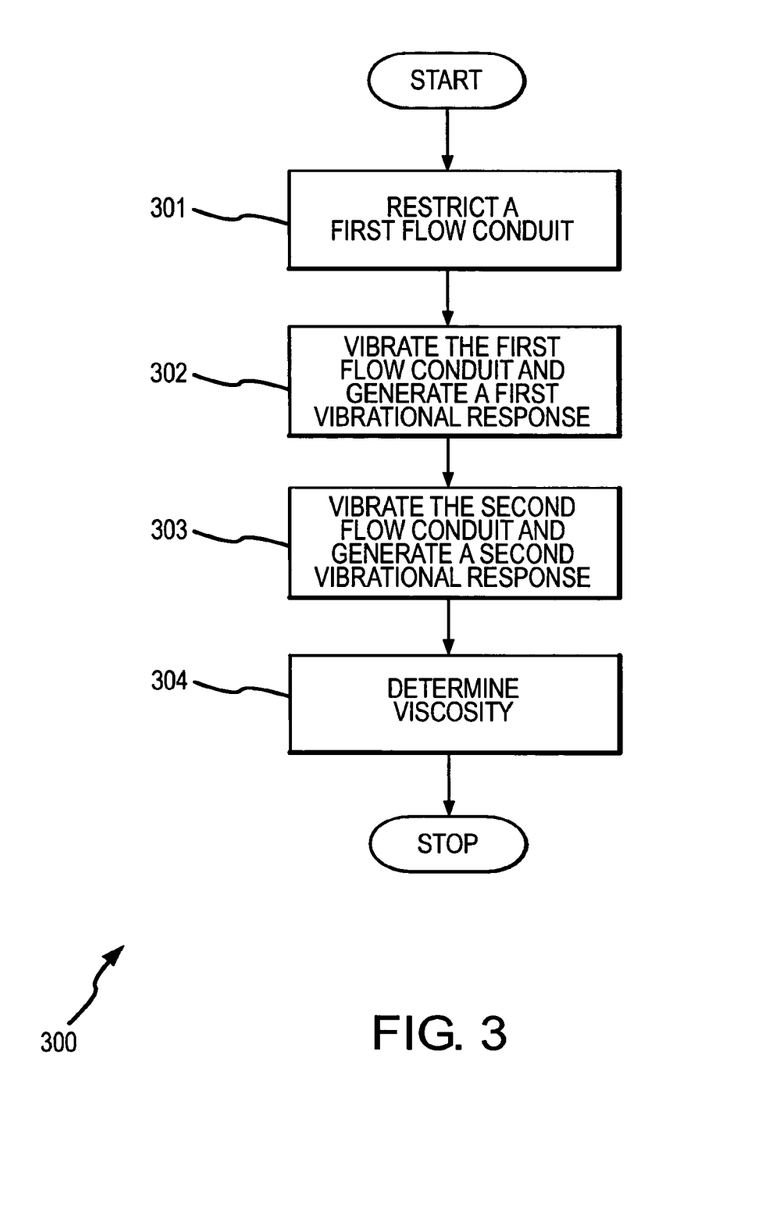
FIG. 3 is a flowchart of a method of determining a viscosity of a flow material in a vibratory flow meter according to an embodiment of the invention.

FIG. 3 is a flowchart 300 of a method of determining a viscosity of a flow material in a vibratory flow meter according to an embodiment of the invention. In step 301, a first flowtube is restricted in order to cause an unrecovered kinetic energy loss through turbulence generated by the restriction. Because of the restriction in the first flowtube, the first flow rate through the first flowtube is less than the second flow rate of the flow material through the second flowtube.

In step 302, the first flowtube is vibrated and a first vibrational response is generated. The first vibrational response comprises a response to the vibration of the flowtubes of the meter assembly 200.

In step 303, the second flowtube is vibrated and a second vibrational response is generated. The second flowtube is vibrated in conjunction with the first flowtube and substantially simultaneously, such as by a common driver, for example. The second vibrational response comprises a response to the vibration of the flowtubes of the meter assembly 200.

In step 304, the viscosity of the flow material is determined. The viscosity can be determined from the first vibrational response and the second vibrational response. More specifically, the viscosity can be determined from a determined flow material density ($\rho$), from a determined first flow rate ($\dot{m}_1$) of the first flow, and a determined second flow rate ($\dot{m}_2$) of the second flow. The flow material density ($\rho$), the first flow rate ($\dot{m}_1$), and the second flow rate ($\dot{m}_2$) can be determined from the first and second vibrational responses, as previously discussed.

Figure 4:
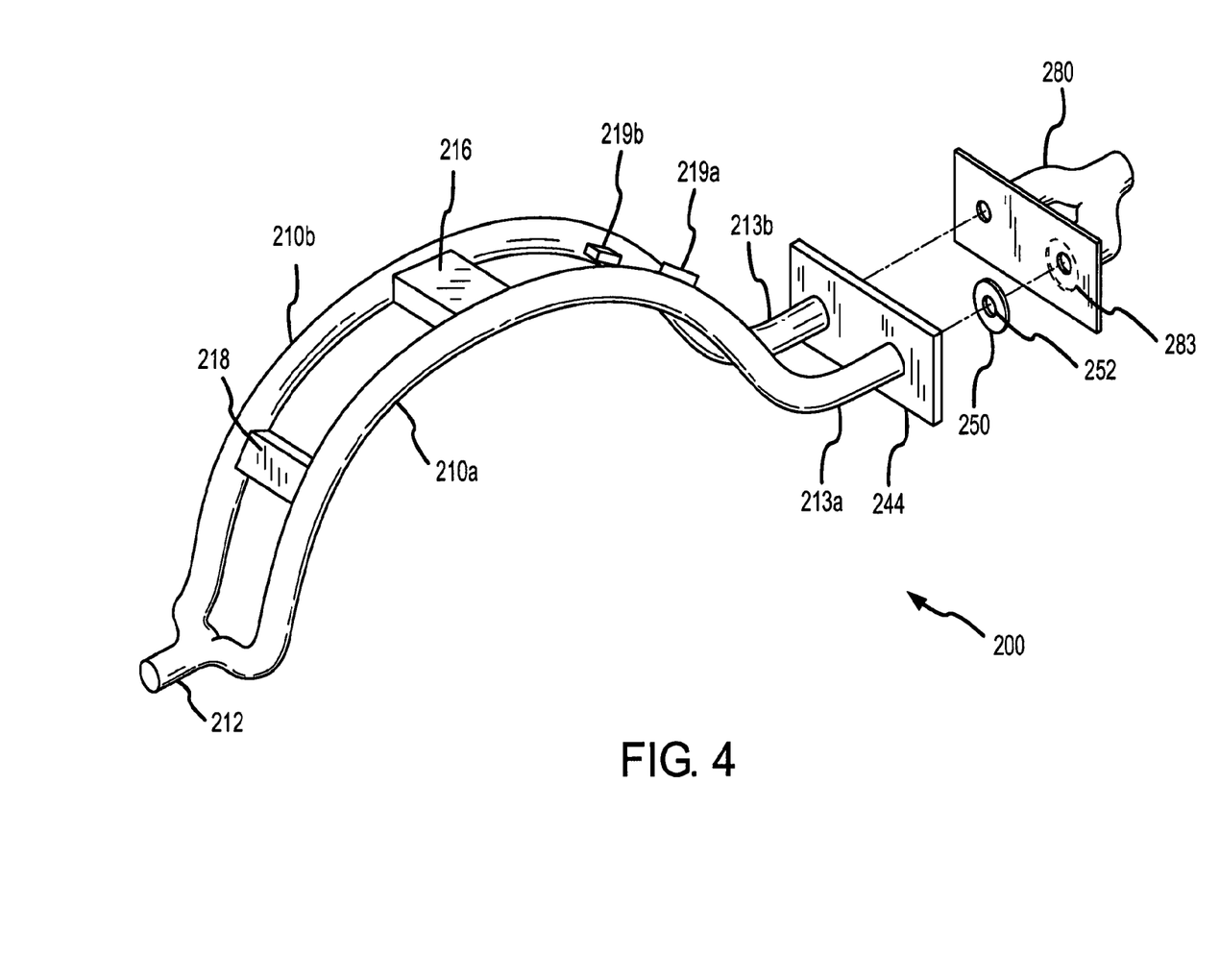
FIG. 4 shows the vibratory flow meter according to an embodiment of the invention.

FIG. 4 shows the meter assembly 200 according to an embodiment of the invention. Elements in common with other embodiments share reference numbers. The meter assembly 200 of this embodiment includes a common flange 244. Both the first flowtube 210a and the second flowtube 210b are terminated in the flange 244. The meter assembly 200 of this embodiment can further include an output manifold 280 that connects to the common flange 244. A removable orifice plate 250 can be compressed or otherwise held between the flange 244 and the output manifold 280. The removable orifice plate 250 can include at least one restrictive orifice 252, as previously discussed. As previously disclosed, the restrictive orifice 252 is less than the local conduit diameter.

As shown in the figure, the removable orifice plate 250 can communicate with only one flowtube. However, it should be understood that the removable orifice plate 250 can alternatively include a second orifice that communicates with the other flowtube. In the alternative orifice plate including two orifices, one orifice must be smaller than the other in order to create different flow rates between the two flowtubes.

One or both of the flange 244 and the output manifold 280 can include a chamber or countersink 283 that receives the removable orifice plate 250. Consequently, the removable orifice plate 250 is retained between the flange 244 and the output manifold 280. The removable orifice plate 250 can be at least partially compressed between the flange 244 and the output manifold 280 in embodiments where the removable orifice plate 250 is at least partially compressible. Alternatively, the removable orifice plate 250 can be clamped between the flange 244 and the output manifold 280.

Figure 5:
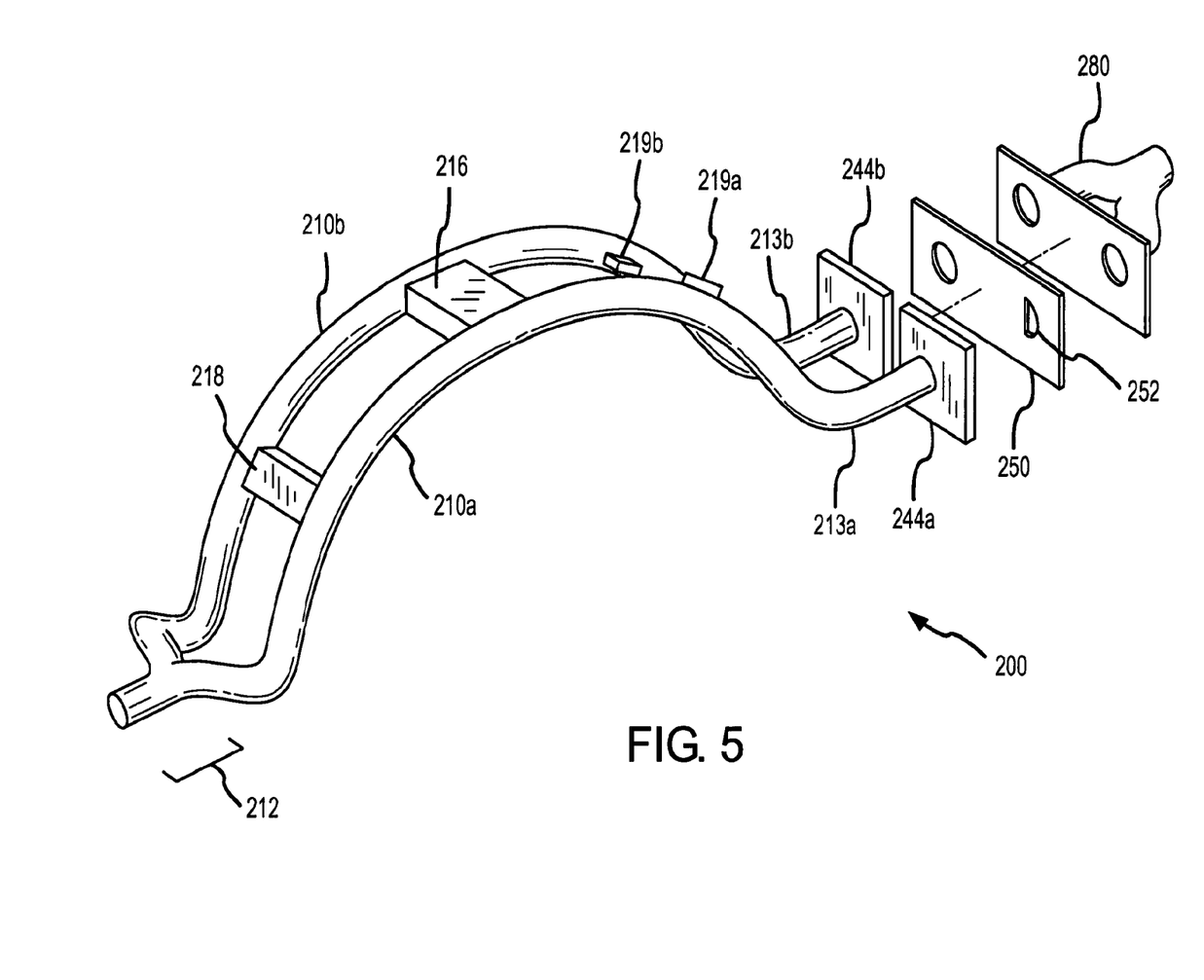
FIG. 5 shows the vibratory flow meter according to an embodiment of the invention.

FIG. 5 shows the meter assembly 200 according to an embodiment of the invention. In this embodiment, the restrictive orifice 252 is non-circular. In this embodiment, the restrictive orifice 252 comprises a semi-circular orifice 252.

It should be understood that any orifice shape can be employed. The only condition on the restrictive orifice 252 is that it produces a non-recoverable energy loss. Consequently, the restrictive orifice 252 cannot comprise a venturi or other restriction that recovers the kinetic energy and converts it back to pressure.

Figure 6:
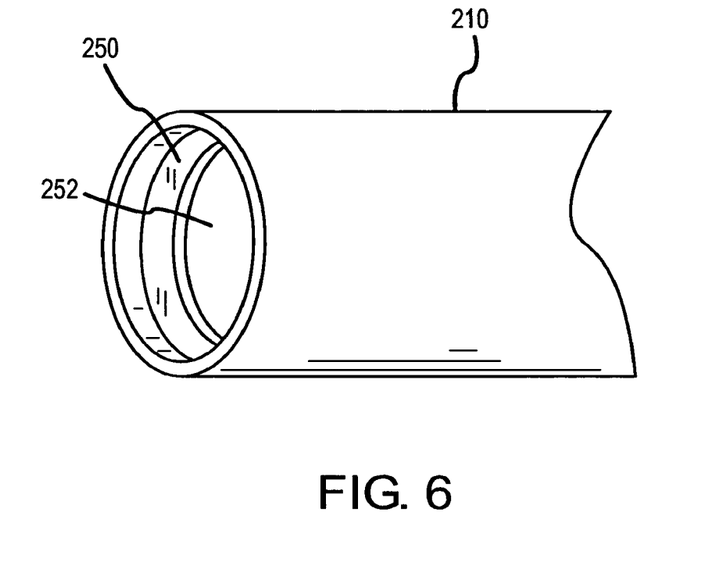
FIG. 6 shows a portion of a flowtube according to an embodiment of the invention.

FIG. 6 shows a portion of a flowtube 210 according to an embodiment of the invention. In this embodiment, a removable orifice member 250 is positioned inside the flowtube 210. The removable orifice member 250 includes a restrictive orifice 252, as previously discussed. The removable orifice member 250 can be installed into and removed from the flowtube 210.

In some embodiments, the removable orifice member 250 can be held in position by a feature of the flowtube 210. For example, the removable orifice member 250 can be held in position by a bend in the flowtube 210. Alternatively, the removable orifice member 250 can be held in position by a narrowing or change in shape of the flowtube 210. In another alternative, the removable orifice member 250 can be held in position by other fasteners, including springs or other biasing members, etc. For example, the removable orifice member 250 can comprise a substantially helical strip of material that can be at least partially radially compressed for insertion or removal. In yet another alternative, the removable orifice member 250 can be held in position by friction.

In another embodiment, the removable orifice member 250 can comprise a portion of the flowtube 210 or can be fixed in the flowtube 210. For example, the restrictive orifice 252 can comprise a weld bead extending at least partially around an interior of the flowtube to form the restrictive orifice 252. However, it should be understood that the restrictive orifice can be formed in other ways.

Figure 7:
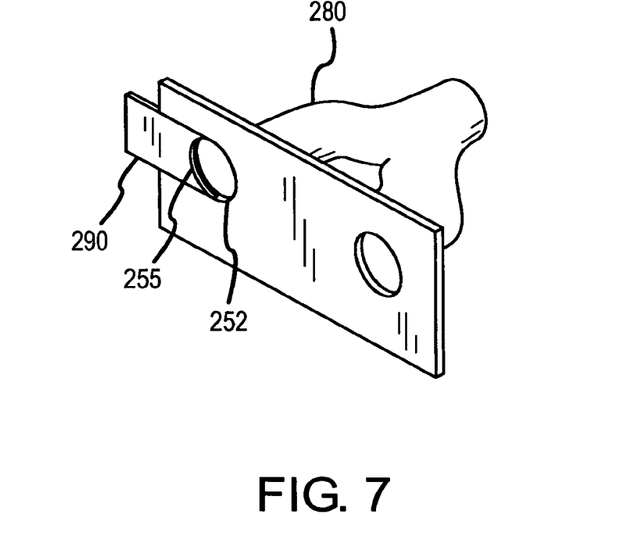
FIG. 7 shows the output manifold according to an embodiment of the invention.

FIG. 7 shows the output manifold 280 according to an embodiment of the invention. In this embodiment, the restrictive orifice 252 is formed in the manifold 280 and comprises a controllable orifice member 290. However, it should be understood that the controllable orifice member 290 can alternatively be formed in a flange 244 or can be positioned between the outlet flange and the outlet manifold, for example. Other controllable orifice members 290 are contemplated and are within the scope of the description and claims.

The controllable orifice member 290 is movable to create a restrictive orifice 252 of varying sizes. The controllable orifice member 290 can be actuated as needed and in order to create a restrictive orifice 252 as desired.

The controllable orifice member 290 in the embodiment shown is configured to slide in order to make the restrictive orifice 252 larger or smaller. However, the controllable orifice member 290 can be configured to move in other manners.

The controllable orifice member 290 in the embodiment shown includes a curved end 255 that maintains an approximately circular restrictive orifice 252. However, the end 255 can include any shape and does not have to maintain a circular restrictive orifice 252.

In some embodiments, the controllable orifice member 290 can be electrically actuated, wherein the controllable orifice member 290 can be moved to enlarge or restrict the size of the restrictive orifice 252. In such an embodiment, the controllable orifice member 290 can be movable by the meter electronics 20, wherein the meter electronics 20 can optionally control the size and/or shape of the restrictive orifice 252.

Figure 8:
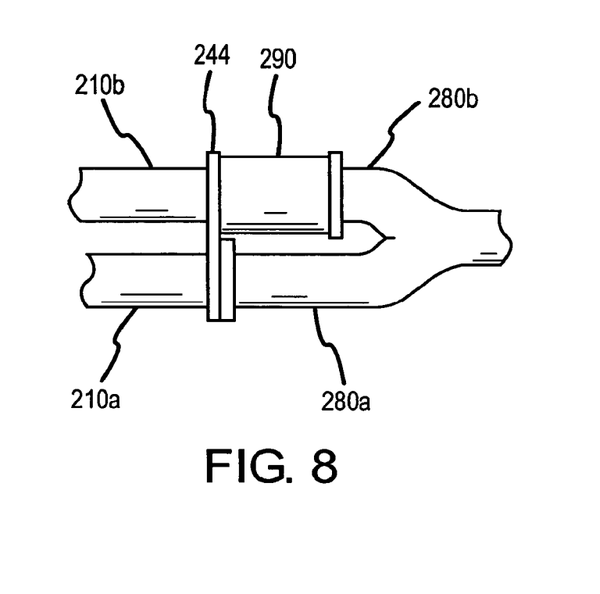
FIG. 8 shows a portion of the flow meter according to an embodiment of the invention.

FIG. 8 shows a portion of the meter assembly 200 according to an embodiment of the invention. The figure shows a common flange 244 and a portion of conduits 280a and 280b (or an outlet manifold 280) connected to the flange 244. It should be understood that alternatively the meter assembly 200 can include separate flanges 244a and 244b as shown in FIG. 2. The meter assembly 200 in this embodiment includes a controllable orifice member 290, such as a valve, for example. The controllable orifice member 290 can be in communication with at least one of the flowtubes. The controllable orifice member 290 can be actuated in order to provide (and modify) the restrictive orifice 252.

In one embodiment, the controllable orifice member 290 can be actuated by the meter electronics 20. The meter electronics 20 can select a controllable orifice member position and therefore a restrictive orifice size. The meter electronics 20 can select a controllable orifice member position based on an anticipated or pre-designated flow material viscosity. In addition, the meter electronics 20 can perform any manner of convergence algorithm and therefore can actuate the controllable orifice member 290 according to an actual or anticipated viscosity of the flow material.

Advantageously, in some embodiments the controllable orifice member 290 can be moved over a substantially continuous range of valve positions. The controllable orifice member 290 can move to a fully closed or nearly fully closed position. The controllable orifice member 290 can move to a fully or nearly fully opened position.

Figure 9:
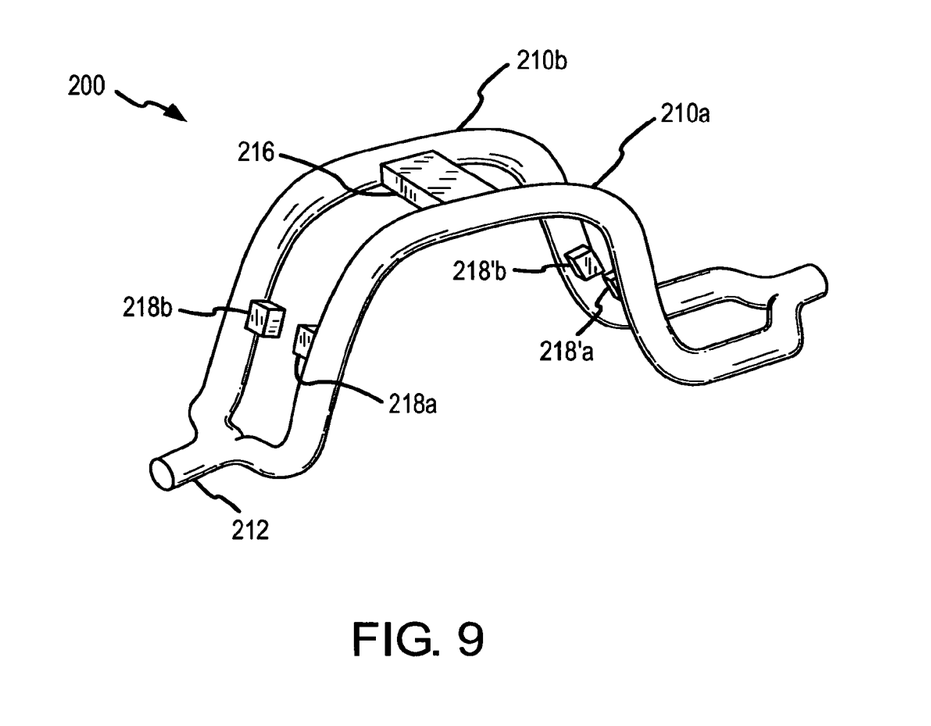
FIG. 9 shows the vibratory flow meter according to an embodiment of the invention.

FIG. 9 shows the meter assembly 200 according to an embodiment of the invention. In this embodiment, the first flowtube 210a includes a pair of first pickoff sensors 218a and 218'a that are positioned to detect vibration of the first flowtube 210a. The second flowtube 210b includes a pair of second pickoff sensors 218b and 218'b that are positioned to detect vibration of the second flowtube 210b. The first pickoff sensors 218a and 218'a and the second pickoff sensors 218b and 218'b can be supported by any manner of rigid support structure (not shown), wherein the pickoff sensor is held in a fixed position by the support structure and measures relative motion of the vibration of the corresponding flowtube. However, the support structure for the first pickoff sensors 218a and 218'a can be the same or different than the support structure employed for the second pickoff sensors 218b and 218'b. Upon vibration of the flowtubes 210a and 210b, the pair of first pickoff sensors 218a and 218'a generate a flow characteristic measurement for the first flowtube 210a and the pair of second pickoff sensors 218b and 218'b generate a flow characteristic measurement for the second flowtube 210b.

Figure 10:
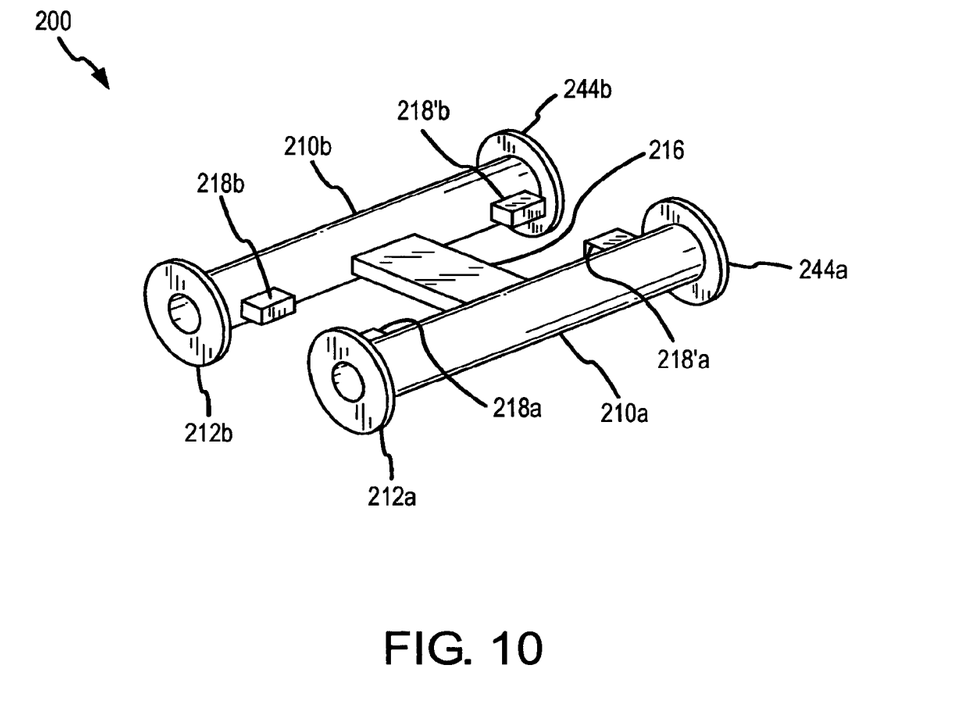
FIG. 10 shows a straight tube vibratory flow meter according to an embodiment of the invention.

FIG. 10 shows a straight tube meter assembly 200 according to an embodiment of the invention. In this embodiment, the flowtubes 210a and 210b are substantially straight. It should be understood that the meter assembly 200 of this embodiment can include one shared pickoff as in FIG. 2 or can include two independent sets of pickoffs as in FIG. 9.

The vibratory flow meter and method according to the invention can be employed according to any of the embodiments in order to provide several advantages, if desired. The vibratory flow meter according to the invention can be operated as a viscometer. The vibratory flow meter and method enables a vibratory flow meter to measure the viscosity of a flow material. The vibratory flow meter and method enables a viscometer to be quickly and easily configured for a particular flow material. The vibratory flow meter and method enables a viscometer to be quickly and easily re-configured for a new flow material.

What is claimed is:

1. A vibratory flow meter (5) for determining a viscosity of a flow material, being characterized by:
   a meter assembly (200) configured to generate a first vibrational response in a first flowtube (210a) and generate a second vibrational response in a second flowtube (210b);
   a common driver (104) configured to substantially simultaneously vibrate the first flowtube (210a) and the second flowtube (210b) to generate the first vibrational response and the second vibrational response;
   a changeable restrictive orifice (252) located in the first flowtube (210a), wherein the restrictive orifice (252) ensures that a first flow rate of the flow material in the first flowtube (210a) is less than a second flow rate of the flow material in the second flowtube (210b); and
   meter electronics (20) coupled to the meter assembly (200) and configured to determine the viscosity of the flow material from the first vibrational response and the second vibrational response, the meter assembly (200) including three pickoff sensors (218) configured to generate a first vibrational response from the first flowtube (210a) and a second vibrational response from the second flowtube (210b), wherein one of the three pickoff sensors (218) is shared between the first flowtube (210a) and the second flowtube (210b); and
   wherein the three pickoff sensors (218) are configured to generate a first independent vibrational response using the shared pickoff sensor and a first independent pickoff sensor of the three pickoff sensors, and to generate a second independent vibrational response using the shared pickoff sensor and a second independent pickoff sensor of the three pickoff sensors.

2. The vibratory flow meter (5) of claim 1, with the changeable restrictive orifice (252) being selected for a predetermined flow material viscosity range.

3. The vibratory flow meter (5) of claim 1, with the vibratory flow meter (5) comprising a viscometer.

4. The vibratory flow meter (5) of claim 1, further comprising a second restrictive orifice (252b) located in the second flowtube (210b), with the second restrictive orifice (252b) being different from the changeable restrictive orifice (252).

5. The vibratory flow meter (5) of claim 1, with the meter electronics (20) configured to determine a flow material density ($\rho$), a first mass flow rate ($\dot{m}_1$), and a second mass flow rate ($\dot{m}_2$) from the first vibrational response and the second vibrational response.

6. The vibratory flow meter (5) of claim 5, further comprising determining the viscosity of the flow material from the flow material density ($\rho$), the first mass flow rate ($\dot{m}_1$) of the first flow, and the second mass flow rate ($\dot{m}_2$) of the second flow.

7. The vibratory flow meter (5) of claim 1, with the changeable restrictive orifice (252) being formed in a removable orifice member (250).

8. A vibratory flow meter (5) for determining a viscosity of a flow material, comprising:
- a meter assembly (200) configured to generate a first vibrational response in a first flowtube (210a) and generate a second vibrational response in a second flowtube (210b);
- a common driver (104) configured to substantially simultaneously vibrate the first flowtube (210a) and the second flowtube (210b) to generate the first vibrational response and the second vibrational response;
- three pickoff sensors (218) configured to generate the first vibrational response from the first flowtube (210a) and the second vibrational response from the second flowtube (210b), wherein one of the three pickoff sensors (218) is shared between the first flowtube (210a) and the second flowtube (210b), wherein the three pickoff sensors (218) are configured to generate a first independent vibrational response using the shared pickoff sensor and a first independent pickoff sensor of the three pickoff sensors, and to generate a second independent vibrational response using the shared pickoff sensor and a second independent pickoff sensor of the three pickoff sensors;
- a changeable restrictive orifice (252) located in the first flowtube (210a), with the changeable restrictive orifice (252) being smaller than a local flowtube diameter and with the changeable restrictive orifice (252) ensuring that a first flow rate of the flow material in the first flowtube (210a) is less than a second flow rate of the flow material in the second flowtube (210b); and
- meter electronics (20) coupled to the common driver (104) and the three pickoff sensors (218) and configured to determine the viscosity of the flow material from the first vibrational response and the second vibrational response.

9. The vibratory flow meter (5) of claim 8, with the changeable restrictive orifice (252) being selected for a predetermined flow material viscosity range.

10. The vibratory flow meter (5) of claim 8, with the vibratory flow meter (5) comprising a viscometer.

11. The vibratory flow meter (5) of claim 8, further comprising a second restrictive orifice (252b) located in the second flowtube (210b), with the second restrictive orifice (252b) being different from the changeable restrictive orifice (252).

12. The vibratory flow meter (5) of claim 8, with the meter electronics (20) configured to determine the viscosity of the flow material from the first vibrational response and the second vibrational response.

13. The vibratory flow meter (5) of claim 12, with determining the viscosity of the flow material from the first vibrational response and the second vibrational response comprising determining the viscosity from a flow material density ($\rho$), a first mass flow rate ($\dot{m}_1$) of the first flow, and a second mass flow rate ($\dot{m}_2$) of the second flow.

14. The vibratory flow meter (5) of claim 8, with the changeable restrictive orifice (252) being formed in a removable orifice member (250).

15. The vibratory flow meter (5) of claim 8, with the changeable restrictive orifice (252) comprising an adjustable restrictive orifice (252) of a controllable orifice member (290).

16. A vibratory flow meter (5) for determining a viscosity of a flow material, comprising:
- a meter assembly (200) configured to generate a first vibrational response in a first flowtube (210a) and generate a second vibrational response in a second flowtube (210b);
- a common driver (104) configured to substantially simultaneously vibrate the first flowtube (210a) and the second flowtube (210b) to generate the first vibrational response and the second vibrational response;
- three pickoff sensors (218) configured to generate the first vibrational response from the first flowtube (210a) and the second vibrational response from the second flowtube (210b), wherein one of the three pick-off sensors is shared between the first flow tube (210a) and the second flow tube (210b), and wherein the three pickoff sensors (218) are configured to generate a first independent vibrational response using the shared pickoff sensor and a first independent pickoff sensor of the three pickoff sensors, and to generate a second independent vibrational response using the shared pickoff sensor and a second independent pickoff sensor of the three pickoff sensors;
- a removable orifice member (250) located in the first flowtube (210a) and including a restrictive orifice (252), with the restrictive orifice (252) being smaller than a local flowtube diameter and with the restrictive orifice (252) ensuring that a first flow rate of the flow material in the first flowtube (210a) is less than a second flow rate of the flow material in the second flowtube (210b); and
- meter electronics (20) coupled to the common driver (104) and the three or more pickoff sensors (218) and configured to determine the viscosity of the flow material from the first vibrational response and the second vibrational response.

17. The vibratory flow meter (5) of claim 16, with the restrictive orifice (252) being selected for a predetermined flow material viscosity range.

18. The vibratory flow meter (5) of claim 16, with the vibratory flow meter (5) comprising a viscometer.

19. The vibratory flow meter (5) of claim 16, further comprising a second restrictive orifice (252b) located in the second flowtube (210b), with the second restrictive orifice (252b) being different from the restrictive orifice (252).

20. The vibratory flow meter (5) of claim 16, with the meter electronics (20) configured to determine the viscosity of the flow material from the first vibrational response and the second vibrational response.

21. The vibratory flow meter (5) of claim 20, with determining the viscosity of the flow material from the first vibrational response and the second vibrational response comprising determining the viscosity from a flow material density ($\rho$), a first mass flow rate ($\dot{m}_1$) of the first flow, and a second mass flow rate ($\dot{m}_2$) of the second flow.

22. A vibratory flow meter (5) for determining a viscosity of a flow material, comprising:

a meter assembly (200) configured to generate a first vibrational response in a first flowtube (210a) and generate a second vibrational response in a second flowtube (210b);

a common driver (104) configured to substantially simultaneously vibrate the first flowtube (210a) and the second flowtube (210b) to generate the first vibrational response and the second vibrational response;

three pickoff sensors (218) configured to generate the first vibrational response from the first flowtube (210a) and the second vibrational response from the second flowtube (210b), wherein one of the three pick-off sensors is shared between the first flow tube (210a) and the second flow tube (210b) and wherein the three pickoff sensors (218) are configured to generate a first independent vibrational response using the shared pickoff sensor and a first independent pickoff sensor of the three pickoff sensors, and to generate a second independent vibrational response using the shared pickoff sensor and a second independent pickoff sensor of the three pickoff sensors a controllable orifice member (290) that provides an adjustable restrictive orifice (252) in communication with the first flowtube (210a), with the adjustable restrictive orifice (252) being smaller than a local flowtube diameter and with the controllable orifice member (290) therefore ensuring that a first flow rate of the flow material in the first flowtube (210a) is less than a second flow rate of the flow material in the second flowtube (210b), wherein the controllable orifice member (290) is controllable to achieve a plurality of orifice configurations; and meter electronics (20) coupled to the common driver (104) and the three or more pickoff sensors (218) and configured to determine the viscosity of the flow material from the first vibrational response and the second vibrational response.

23. The vibratory flow meter (5) of claim 22, with the adjustable restrictive orifice (252) being selected for a predetermined flow material viscosity range.

24. The vibratory flow meter (5) of claim 22, with the vibratory flow meter (5) comprising a viscometer.

25. The vibratory flow meter (5) of claim 22, further comprising a second controllable orifice member (290) in communication with the second flowtube (210b) and including a second adjustable restrictive orifice (252), with the second adjustable restrictive orifice (252) being different from the adjustable restrictive orifice (252).

26. The vibratory flow meter (5) of claim 22, with the meter electronics (20) configured to determine the viscosity of the flow material from the first vibrational response and the second vibrational response.

27. The vibratory flow meter (5) of claim 26, with determining the viscosity of the flow material from the first vibrational response and the second vibrational response comprising determining the viscosity from a flow material density ($\rho$), a first mass flow rate ($\dot{m}_1$) of the first flow, and a second mass flow rate ($\dot{m}_2$) of a second flow.

28. The vibratory flow meter (5) of claim 22, wherein one of the three or more pickoff sensors (218) is shared between the first flowtube (210a) and the second flowtube (210b).

29. A method of determining a viscosity of a flow material in a vibratory flow meter, the method comprising:

partially restricting a first flowtube with a changeable restrictive orifice with the first flowtube conducting a first flow of a flow material and with the second flowtube conducting a second flow of the flow material, with the second flow being different from the first flow;

vibrating a first flowtube of the vibratory flow meter with a common driver and generating a first independent vibrational response using a shared pickoff sensor and a first independent pickoff sensor;

substantially simultaneously vibrating a second flowtube of the vibratory flow meter with the common driver and generating a second independent vibrational response using the shared pickoff sensor and a second independent pickoff sensor wherein the shared pickoff sensor generates a shared vibrational response from the vibration of both the first flowtube and the second flowtube; and a meter electronics receiving the first independent vibrational response and the second independent vibrational response and determining a viscosity of the flow material from the first independent vibrational response and the second independent vibrational response.

30. The method of claim 29, with the vibratory flow meter comprising a viscometer.

31. The method of claim 29, with determining the viscosity of the flow material from the first vibrational response and the second vibrational response comprising determining the viscosity from a flow material density ($\rho$), a first mass flow rate ($\dot{m}_1$) of the first flow, and the second mass flow rate ($\dot{m}_2$) of the second flow.

32. The method of claim 29, with the vibratory flow meter including a changeable restrictive orifice located in the first flowtube, with the changeable restrictive orifice being smaller than a local flowtube diameter and with the changeable restrictive orifice ensuring that the first flow is different from the second flow.

33. The method of claim 32, with the changeable restrictive orifice being selected for a predetermined flow material viscosity range.

34. The method of claim 32, further comprising a second restrictive orifice located in the second flowtube, with the second restrictive orifice being different from the changeable restrictive orifice.

35. The method of claim 32, with the changeable restrictive orifice being formed in a removable orifice member.

36. The method of claim 32, with the changeable restrictive orifice comprising an adjustable restrictive orifice of a controllable orifice member.

* * * * *